United States Patent
Yanagi et al.

(10) Patent No.: US 10,338,057 B2
(45) Date of Patent: Jul. 2, 2019

(54) DEVICE AND METHOD FOR FORMING SAME

(71) Applicant: Hitachi, Ltd., Tokyo (JP)

(72) Inventors: Itaru Yanagi, Tokyo (JP); Kenichi Takeda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 102 days.

(21) Appl. No.: 15/508,072

(22) PCT Filed: Sep. 11, 2014

(86) PCT No.: PCT/JP2014/074063
§ 371 (c)(1),
(2) Date: Mar. 1, 2017

(87) PCT Pub. No.: WO2016/038719
PCT Pub. Date: Mar. 17, 2016

(65) Prior Publication Data
US 2017/0307587 A1    Oct. 26, 2017

(51) Int. Cl.
*G01N 27/447* (2006.01)
*G01N 33/487* (2006.01)
(Continued)

(52) U.S. Cl.
CPC ... *G01N 33/48721* (2013.01); *B81C 1/00087* (2013.01); *B82B 1/001* (2013.01);
(Continued)

(58) Field of Classification Search
CPC ....... G01N 33/48721; G01N 27/44791; G01N 27/3278; B82B 1/001; B82B 3/0019;
(Continued)

(56) References Cited

U.S. PATENT DOCUMENTS

| 8,518,829 | B2 | 8/2013 | Dang et al. |
| 2004/0197898 | A1 | 10/2004 | Nakatani et al. |
| 2014/0262820 | A1* | 9/2014 | Kuan ........................ C25F 3/14 205/665 |

FOREIGN PATENT DOCUMENTS

| JP | D9-135033 A | 5/1997 |
| JP | 11-083798 A | 3/1999 |

(Continued)

OTHER PUBLICATIONS

Machine translation to English of JP 2009-130297, A (Year: 2009).*
(Continued)

*Primary Examiner* — J. Christopher Ball
(74) *Attorney, Agent, or Firm* — Procopio, Cory, Hargreaves & Savitch LLP

(57) ABSTRACT

The membrane of a conventional solid-state nanopore device, which is believed to be promising for understanding the structural characteristics of DNA and determining a nucleotide sequence, has been thick, and the accuracy in determining a nucleotide sequence in the DNA chain has been insufficient. A method characterized by forming a membrane by forming a first film on a first substrate having a surface of Si, then forming a hole in the first film in such a manner that the surface of the first substrate is exposed, then forming a second film on the first film and on the surface of the first substrate and then etching the first substrate with a solution which does not remove the second film.

13 Claims, 11 Drawing Sheets

(51) Int. Cl.
*G01N 27/327* (2006.01)
*B82B 1/00* (2006.01)
*B82B 3/00* (2006.01)
*C12Q 1/6869* (2018.01)
*B81C 1/00* (2006.01)
*B82Y 5/00* (2011.01)
*B82Y 40/00* (2011.01)

(52) U.S. Cl.
CPC .......... *B82B 3/0019* (2013.01); *C12Q 1/6869* (2013.01); *G01N 27/3278* (2013.01); *G01N 27/44791* (2013.01); *B81B 2203/0127* (2013.01); *B82Y 5/00* (2013.01); *B82Y 40/00* (2013.01); *Y10S 977/888* (2013.01); *Y10S 977/89* (2013.01); *Y10S 977/924* (2013.01)

(58) Field of Classification Search
CPC ............ B82B 1/00087; B81C 1/00087; C12Q 1/6869; Y10S 977/89; Y10S 977/924; Y10S 977/888; B81B 2203/0127; B82Y 40/00; B82Y 5/00
See application file for complete search history.

(56) References Cited

FOREIGN PATENT DOCUMENTS

| | | |
|---|---|---|
| JP | 2003-098146 A | 4/2003 |
| JP | 2004-012215 A | 1/2004 |
| JP | 2009-130297 A | 6/2009 |
| WO | 2007/116978 A1 | 10/2007 |

OTHER PUBLICATIONS

International Search Report and Written Opinion for PCT App No. PCT/JP2014/074063 dated Nov. 18, 2014, 9 pgs.
Larkin, J., et al., Slow DNA Transport Through Nanopores in Hafnium Oxide Membranes, ACS Nano, Nov. 26, 2013, 7(11), pp. 10121-10128.
Yenta, K., et al., Differentiation of Short Single-Stranded DNA Homopolymers in Solid-State Nanopores, ACS Nano, May 28, 2013, 7(5), pp. 4629-4636.
Yanagi, I., et al., Fabricating Nanopores with Diameters of sub-1 nm to 3 nm Using Multilevel Pulse-Voltage Injection, Scientific Reports, 2014, 4, 7 pgs.

* cited by examiner

[FIG. 1]
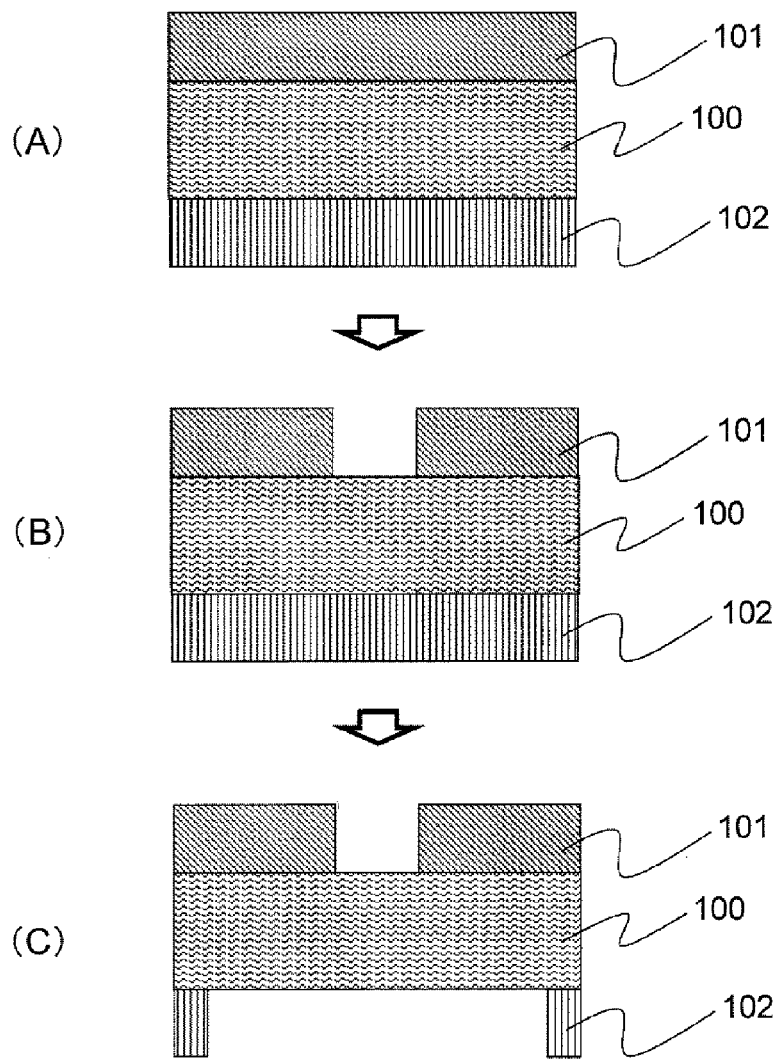

[FIG. 2]
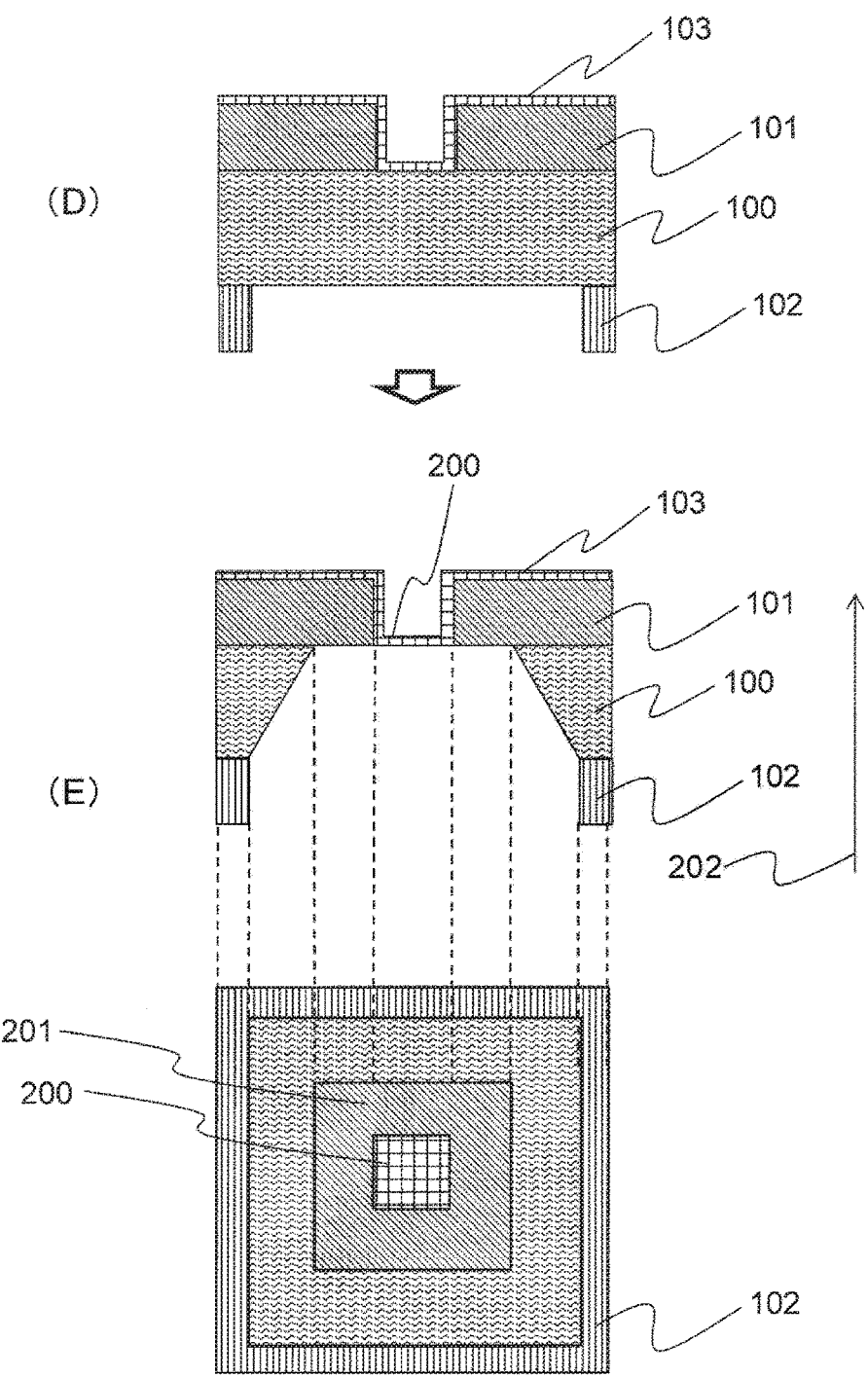

[FIG. 3]
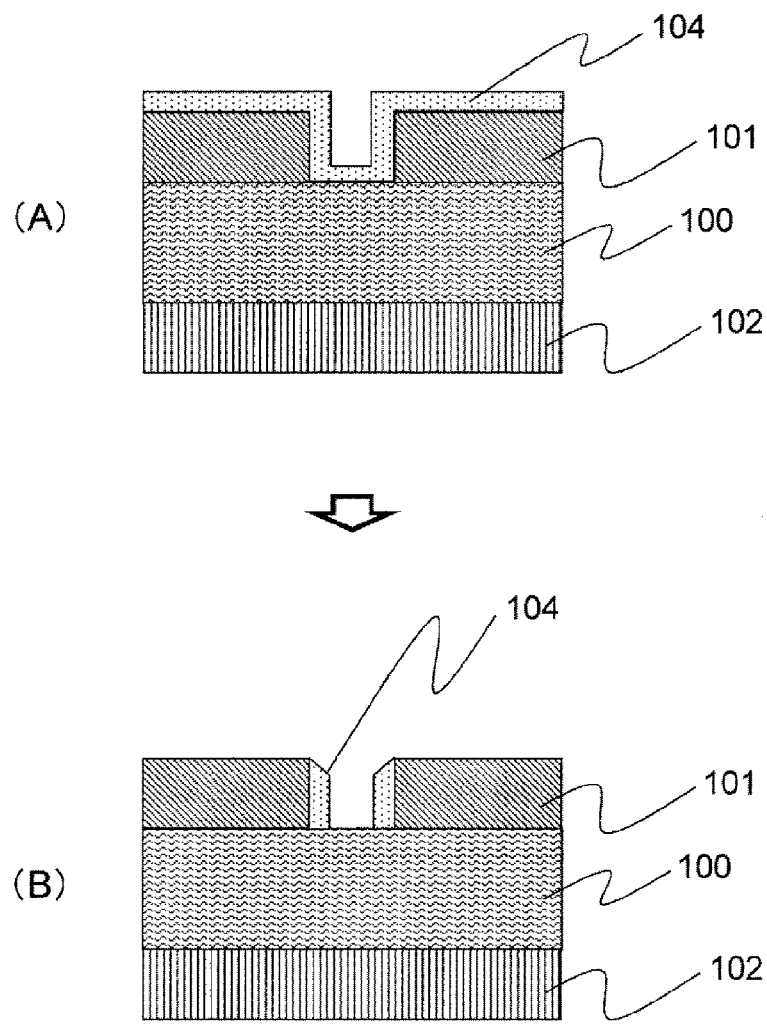

[FIG. 4]
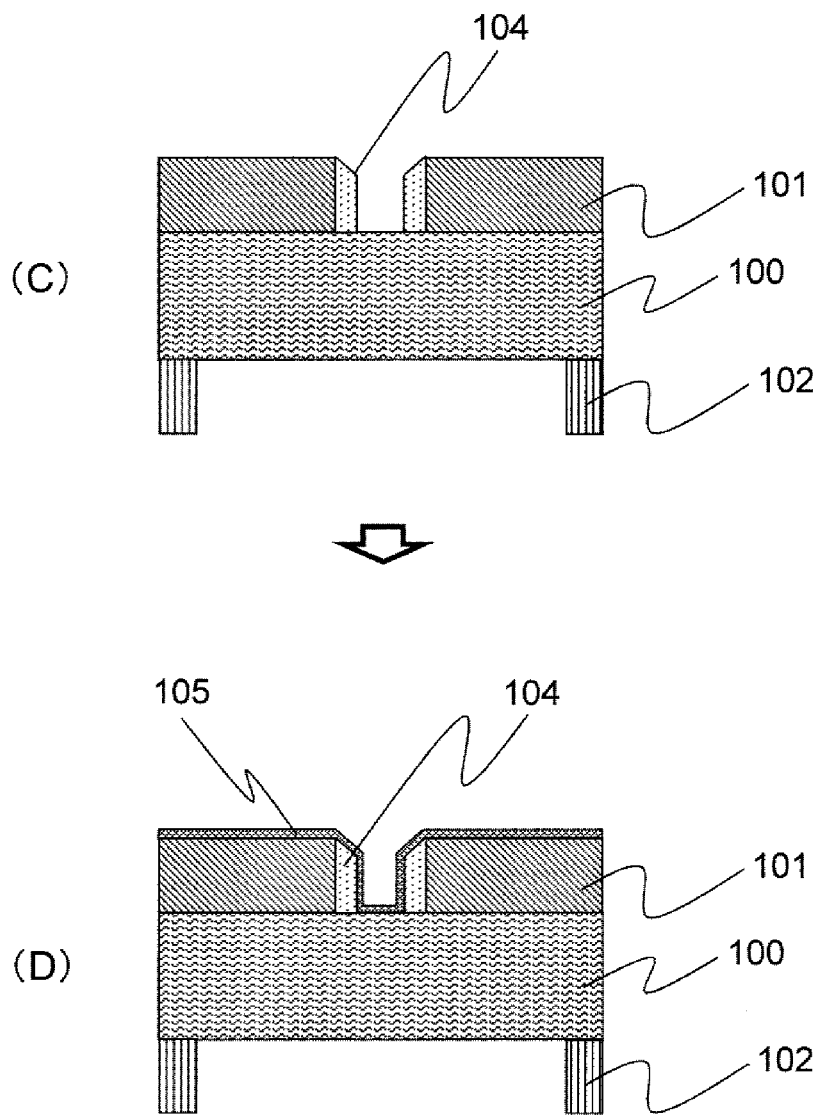

[FIG. 5]
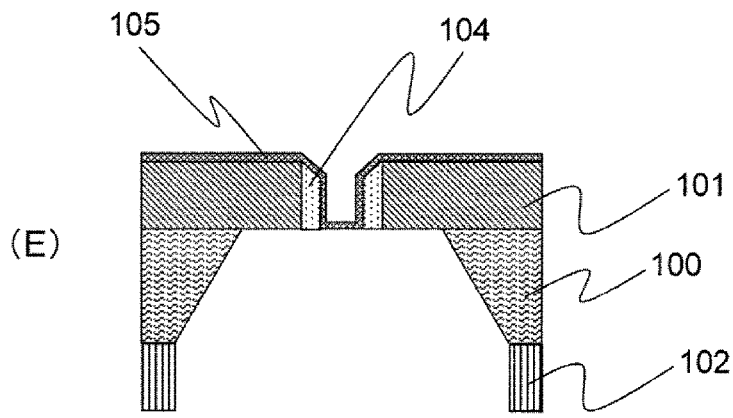
(E)
[FIG. 6]
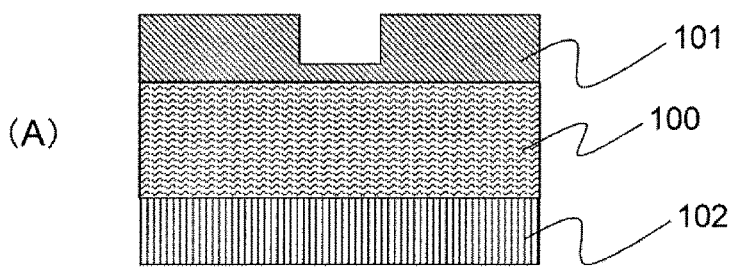
(A)
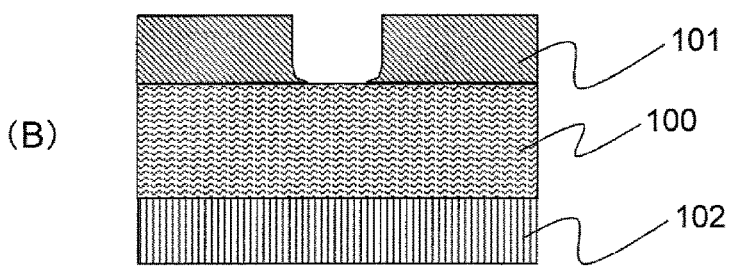
(B)

[FIG. 7]
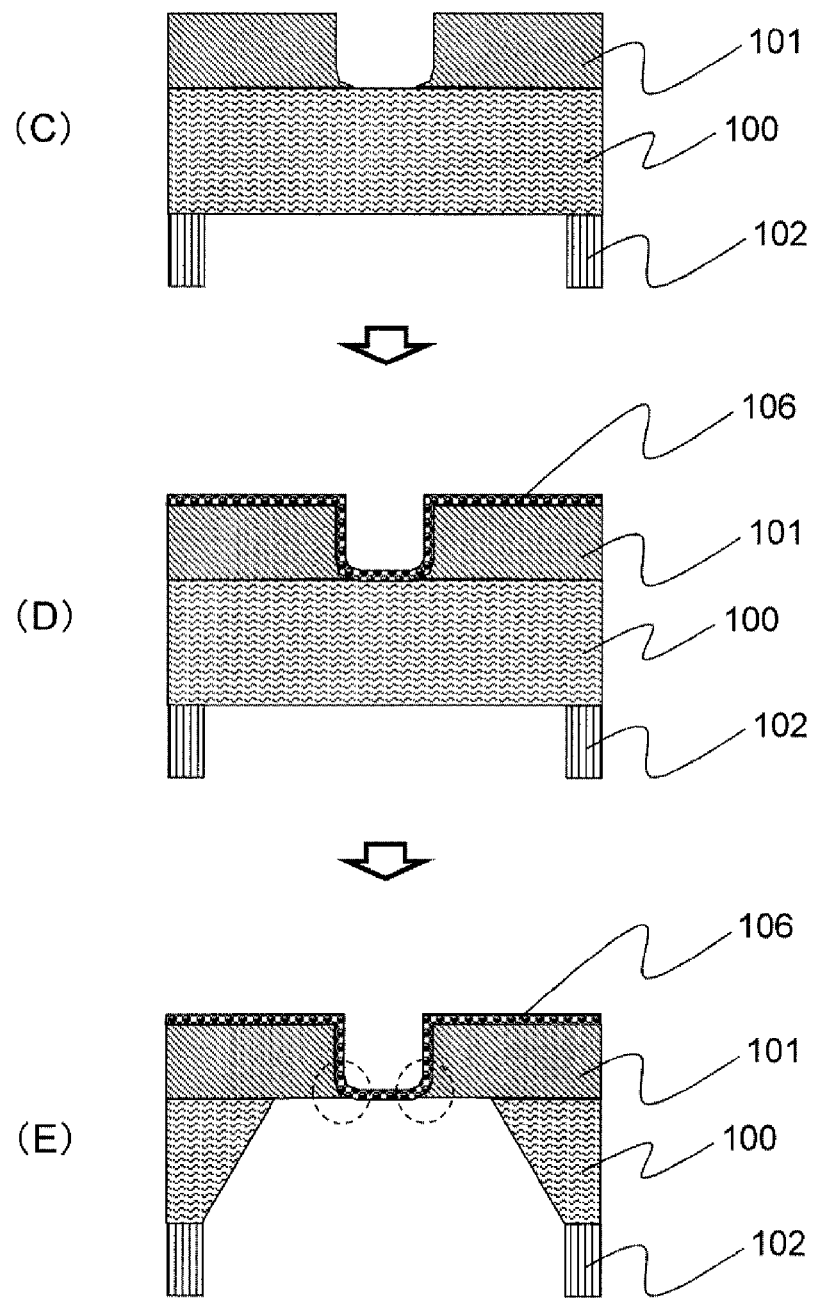

[FIG. 8]
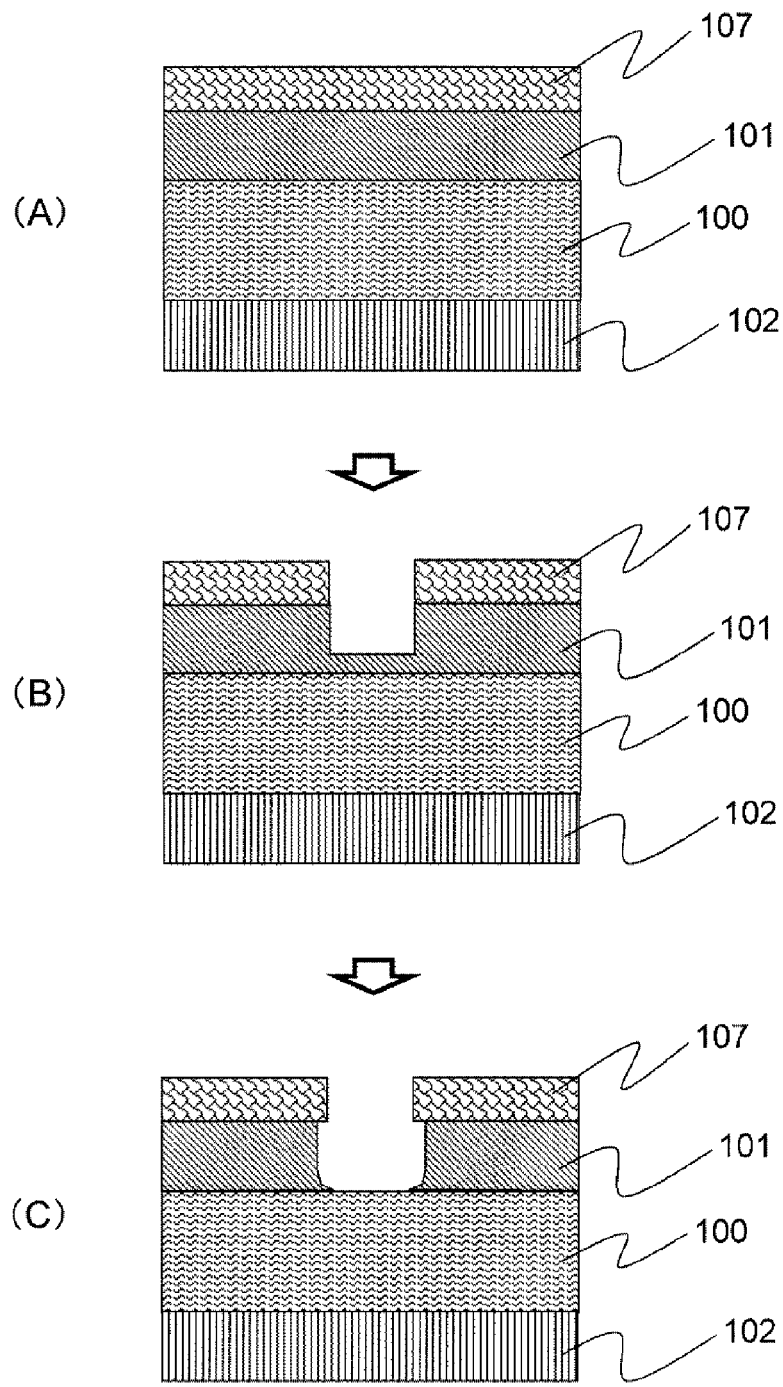

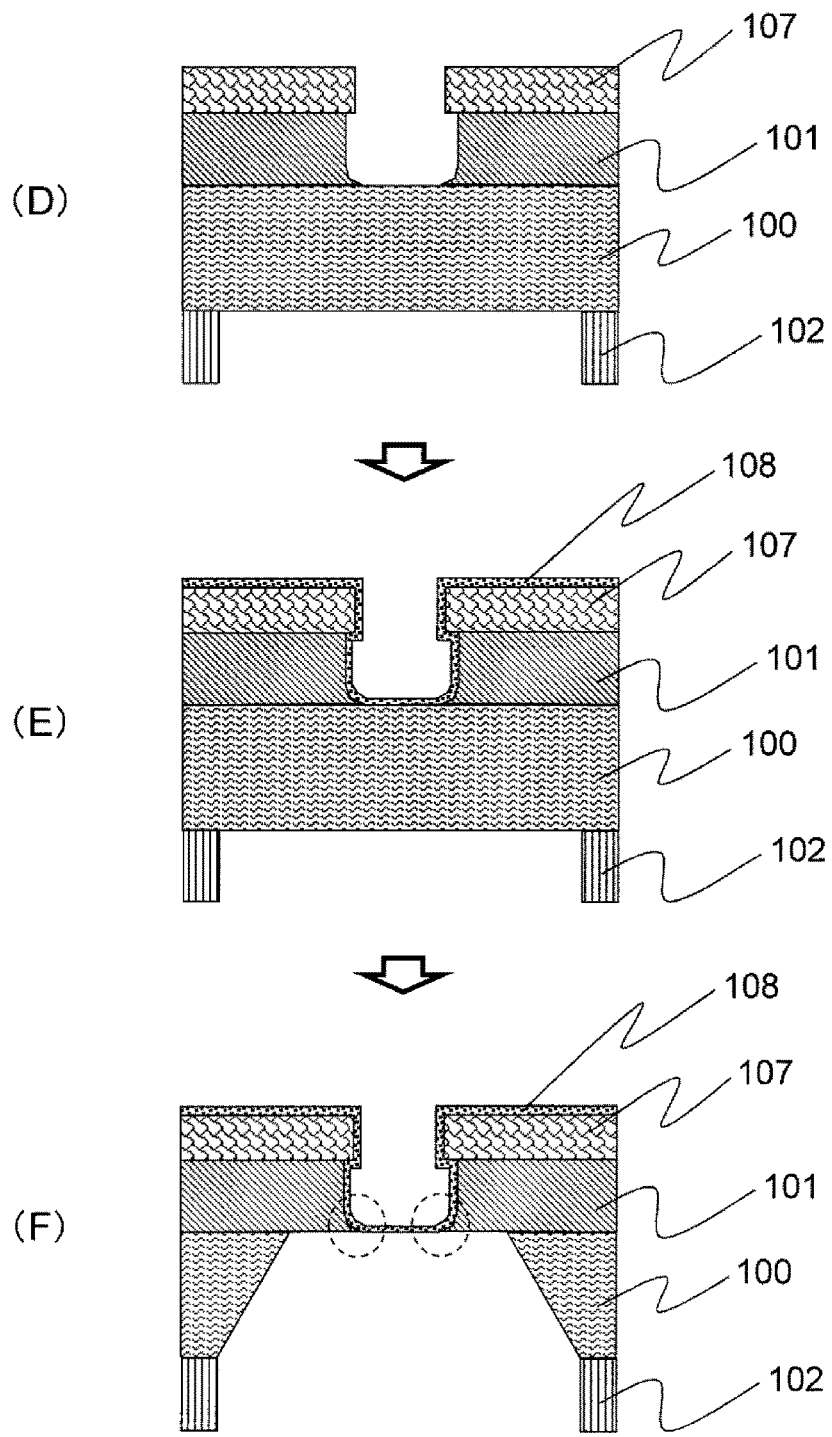
[FIG. 9]

[FIG. 10]
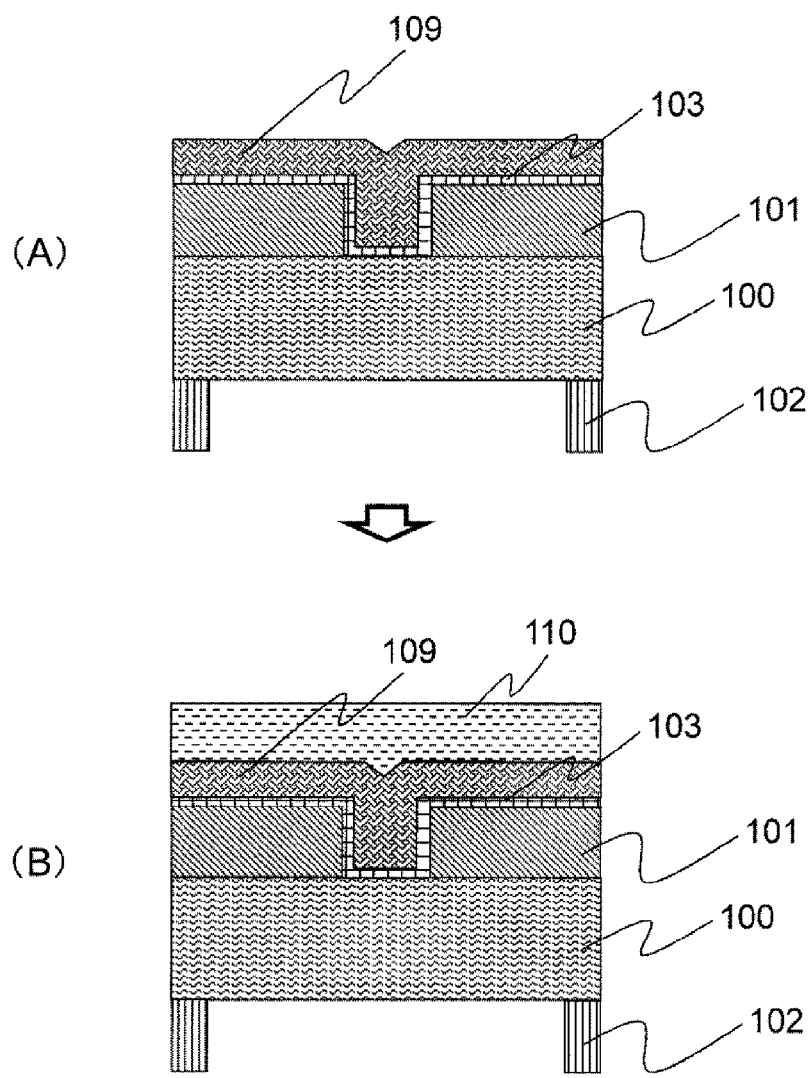

[FIG. 11]
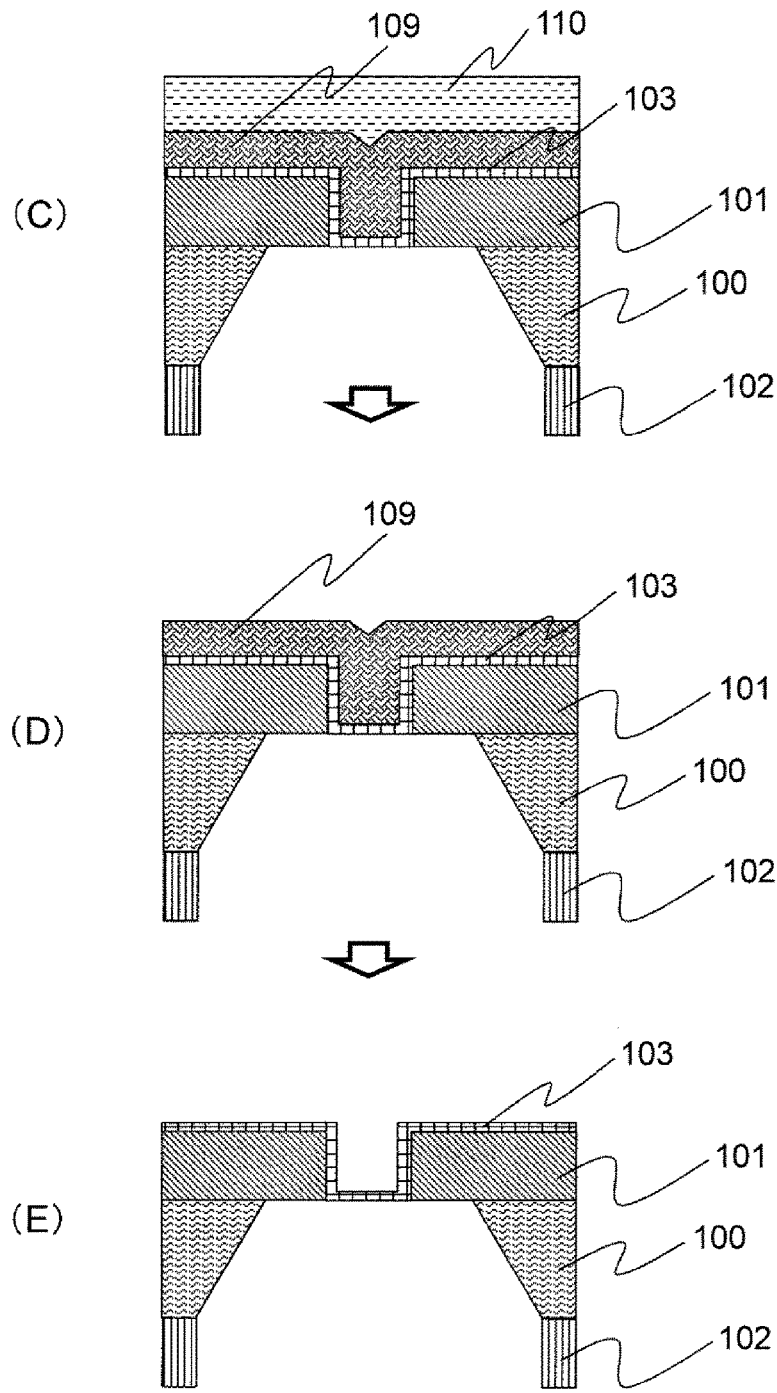

[FIG. 12]
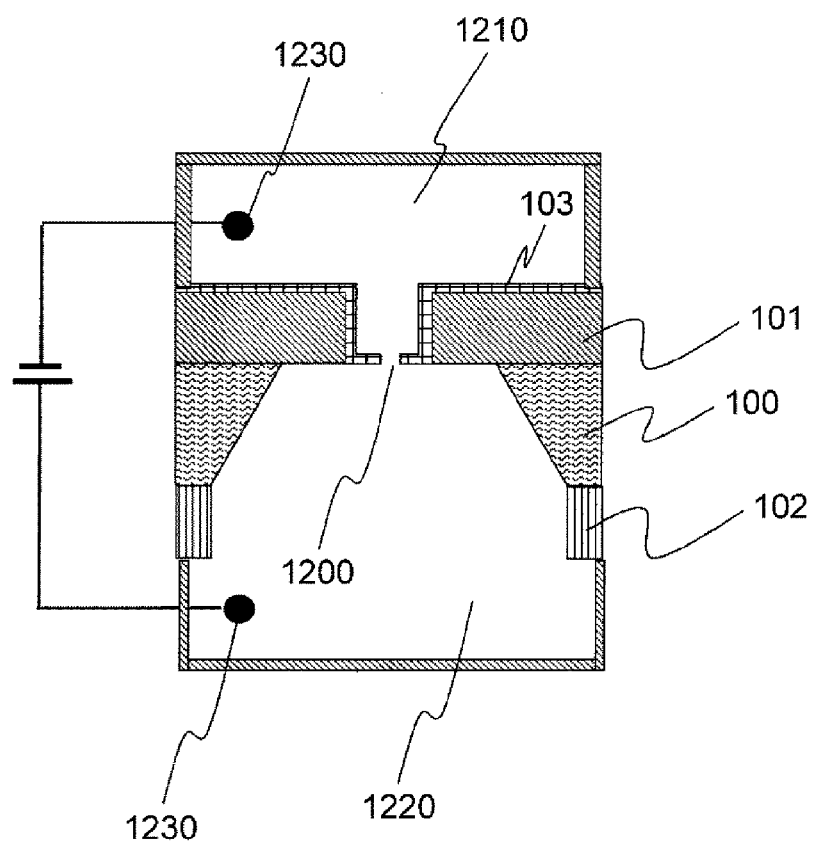

DEVICE AND METHOD FOR FORMING SAME

CROSS-REFERENCE TO RELATED APPLICATIONS

This application is a U.S. National Stage entry of PCT Application No. PCT/JP2014/074063, filed on Sep. 11, 2014, the contents of which are incorporated by reference.

TECHNICAL FIELD

The present invention is a technique related to formation of a membrane. In particular, the technique is suitable for producing a sensor device having a membrane to which a technique for producing a semiconductor is applied.

BACKGROUND ART

As an approach to development of third generation DNA sequencers, a technique using a nanopore has been studied. Specifically, the technique is as follows. A hole having a size equivalent to that of DNA (nanopore) is provided in a thin film membrane, and the chambers above and below the thin film membrane are filled with an aqueous solution. Electrodes are provided in the chambers in such a manner that the electrodes are in contact with the aqueous solution, and DNA to be measured is supplied to one of the chambers. The DNA is moved by electrophoresis caused by a potential difference applied between the electrodes in the chambers so that the DNA passes through the nanopore. By measuring the change with time in the ion current flowing between the electrodes, the structural characteristics of the DNA and the nucleotide sequence are determined. This technique is effective in obtaining the structural characteristics of not only DNA but also of various biomolecules.

To produce a nanopore device, methods using a semiconductor substrate, a semiconductor material and a semiconductor process draw attention due to the high mechanical strength and the like. For example, a thin film membrane can be formed using a silicon nitride film (SiN film). A nanopore can be formed because a small pinhole can be created in a membrane by applying voltage stress to the membrane in an aqueous ionic solution and causing dielectric breakdown (NPL 1). In another method, a nanopore can be formed by etching a membrane using the condensed electron beam.

One of the important factors that determine the accuracy in reading DNA with a nanopore sequencer is the thickness of the membrane. That is, the thinner the membrane is, the better it is. This is because the distance between neighboring bases of the four kinds aligning in a DNA chain is approximately 0.34 nm, and more bases enter the nanopore at the same time as the membrane becomes thicker as compared to the distance. As a result, the signal obtained by measuring the current becomes the signal derived from more than one base. Thus, the accuracy in determining the nucleotide sequence deteriorates, and the analysis of the signal becomes more complex.

CITATION LIST

Patent Literature

PTL 1: U.S. Pat. No. 8,518,829

Non Patent Literature

NPL 1: Yanagi, I., Akahori, R., Hatano, T. & Takeda, K. "Fabricating nanopores with diameters of sub-1 nm to 3 nm using multilevelpulse-voltage injection" Sci. Rep. 4, 5000; DOI:10.1038/srep05000 (2014).

NPL 2: Yenta, K. et al. "Differentiation of short, single-stranded DNA homopolymers in solid-state nanopores" ACS Nano 7, 4629-4636 (2013).

NPL 3: Larkin, J. et al. "Slow DNA Transport through Nanopores in Hafnium Oxide Membranes" ACS Nano 7, 10121-10128 (2013).

SUMMARY OF INVENTION

Technical Problem

To reduce the thickness of a membrane, it is of course preferable that the membrane region is as small as possible. This is because as the membrane region becomes smaller, the possibility of unavoidable defects in the membrane (a weak spot due to the failure of binding between the atoms and the like or a pinhole) which are caused when the membrane is formed becomes lower. Also, it is important to avoid processes which may remove or break the membrane as much as possible when the membrane is formed.

Problems that arise when the thickness of a membrane is to be reduced are explained below while several examples of methods for forming a membrane using a semiconductor material are explained In the simplest production method that the inventors have examined, a membrane supported with a Si substrate can be formed by forming a film serving as a membrane material (for example, SiN) on a Si substrate, forming a film of SiN on the back surface, etching a part of the SiN film on the back surface so that the Si substrate is exposed and then etching the Si substrate with an aqueous KOH or TMAH solution from the part of the exposed Si on the back surface toward the front surface. It is difficult to reduce the area of the membrane by this method. Etching of a Si substrate with an aqueous KOH solution or an aqueous TMAH solution is anisotropic etching in which only a (100) surface is preferentially etched. However, etching of a surface other than a (100) surface also advances, and the variation in shape of etching is large. In particular, because etching advances in unexpected directions from crystal defects in Si, the variation in shape becomes large. Also, the Si substrate that should be etched is usually thick, and the thickness is 100 µm or more (for example, 725 µm in the case of an 8-inch Si wafer). Accordingly, a membrane region having considerably different shape and size from those defined by the mask shape of the SiN film on the back surface is formed. For the above reasons, according to the results of our investigation so far, it is impossible to stably form a membrane with a region of 5 µm×5 µm or less by this production method. However, to form a thin film membrane, the area of the membrane region has to be further reduced.

In another production method, as shown in NPL 1, a SiN membrane can be formed by forming a SiN film on a Si substrate, then forming a $SiO_2$ film on the SiN film, then forming SiN films on the $SiO_2$ and on the back surface of the Si substrate, then patterning a part of the SiN film on top of the front surface of the wafer by dry etching to expose the underlying $SiO_2$ film, then etching a part of the SiN film on the back surface to expose the Si substrate, etching the Si substrate with an aqueous TMAH solution from the back surface and then removing the $SiO_2$ film on the SiN film with an aqueous HF solution. By this method, by forming a hole pattern of for example 100 nm square or smaller using a latest lithography technique and dry etching when a pattern of the SiN is formed on the $SiO_2$, the area of the thinnest region of the membrane (the region of the single SiN membrane layer) can be made around 100-500 nm square including the variation after subsequent etching of the $SiO_2$ with the aqueous HF solution. This point is advantageous in reducing the thickness of the membrane. (However, this is isotropic etching because wet etching is used, and the area of the obtained thin film membrane region unavoidably becomes larger than the area patterned on the SiN because it is impossible to stop etching at the moment when the underlying SiN film is exposed.)

Moreover, the aqueous HF solution also etches the SiN film although the etching rate is lower than that of the $SiO_2$ film. Accordingly, when the aqueous HF solution comes into contact with the SiN membrane of the thin film part, this causes the breakage of the membrane. According to our experimental results, the limit of the thickness of the thinnest part of the membrane obtained by the production method was 7 nm.

As shown in NPL 2, another production method is a method in which a thick SiN membrane is first formed and the thickness of a part thereof is reduced by dry etching. Because the thickness of a limited part of the membrane can be reduced using a latest lithography technique and dry etching by this method, the area of the thin film membrane part can be reduced. However, the dry etching rate varies widely with the process, and the etching rates in the wafer plane also vary widely. Accordingly, the thickness of the obtained membrane varies widely with the process and the sample relative to the target thickness. Also, because ions with high energy collide with the membrane in dry etching, the membrane is damaged. Thus, the very thin film region of the membrane may be broken, and thus the production method is not suitable for reducing the thickness of the membrane, either.

As shown in NPL 3, another production method is a method in which a film of $HfO_2$ is formed on a SiN membrane, then the thickness of a part of the SiN membrane is reduced by dry etching and a thin film membrane of the $HfO_2$ part only is formed. As in NPL 2, because the thickness of a limited part of the membrane can be reduced using a latest lithography technique and dry etching, the area of the thin film membrane part can be reduced. However, because ions with high energy collide with the membrane in dry etching, the membrane is damaged. Thus, the very thin film region of the membrane may be broken, and thus the production method is not suitable for reducing the thickness of the membrane, either.

As shown in PTL 1, another example has a membrane having SiN reinforced with a mechanical support layer on a SOI substrate. When the membrane is formed, the support layer and the $SiO_2$ of the substrate are etched. However, the number of steps increases to form and process the support layer, and etching of the $SiO_2$ without damaging the SiN membrane is difficult. Thus, the example is not suitable for reducing the thickness of the membrane, either.

In the invention, a process and a device structure for achieving the formation of a very thin film membrane which is difficult to achieve with the conventionally known examples are shown. Specifically, a process and a device structure which can make the membrane region as small as possible and which do not damage the membrane when the membrane is formed are shown. Moreover, reduction in the area of the membrane region and formation of a membrane by a process which does not damage the membrane are preferable conditions required for reducing the thickness of the membrane.

Solution to Problem

The present application includes a plurality of means for solving the problems, but examples thereof are as follows.

An aspect of the invention is a method for forming or a method for producing a device characterized by forming a membrane by forming a first film on a surface of a substrate, wherein the surface is Si, then forming a hole in the first film in such a manner that the surface of the substrate is exposed, then forming a second film on the first film and on the surface of the substrate and then etching the substrate with a solution which does not remove the second film.

The device according to another aspect of the invention has a structure having a membrane supported with a substrate in which the surface of the substrate is Si and in which the membrane has a structure in which the substrate is not right under the membrane. The membrane is formed with a film of at least two layers or more, and a part of the membrane has a thin film membrane region formed with a first film. The thin film membrane region is surrounded by a second film which is thicker than the first film. The first film is formed also on a wall of the second film, and the substrate is located right under a part of the second film which is outside the membrane region.

The device according to another aspect of the invention has a laminate structure of a first member and a second member. A first hole is formed through the first member, and a second hole which is smaller than the first hole is formed through the second member at a position which overlaps with the first hole. The structure has a thin film having a thickness of 0.3 nm to 10 nm which is adhered to the surface of the second member opposite to the first member, the surface of the inner wall of the second hole and the inside of the second hole and which is formed to cover the second hole.

As an example of the size, the second hole has a major axis or a length of 100 nm or less. A third hole which is smaller than the second hole is formed through the thin film having a thickness of 0.3 nm to 10 nm formed to cover the second hole. The size of the third hole can be a size of 0.3 nm to 10 nm in the major axis or the length, which is the size of a so-called nanopore.

As preferable materials, the first member is made of Si, and the second member contains SiN or $SiO_2$ at least in a part thereof. The thin film preferably has a thickness of for example 0.3 nm to 10 nm and is made of at least one selected from SiN, $HfO_2$, $HfAlO_x$, $ZrAlO_x$, $Ta_2O_5$, SiC, SiCN and a carbon film or a substance containing at least one selected therefrom. A material that is general as a semiconductor material is SiN. Selecting from the above materials makes it easy to form the first hole through the first member without damaging the other parts. A specific example for forming the first hole through the first member is etching using an aqueous TMAH solution or an aqueous KOH solution. A production method of a device in which the materials and the method are selected to produce the above device is also an aspect of the invention.

Moreover, other aspects of the invention are a sensor using the device and a measurement method using the sensor.

Problems, structures and effects other than those described above are explained by the description of embodiments below.

Advantageous Effects of Invention

Effects obtained by typical embodiments of the invention disclosed in the present application are briefly explained below. That is, an inorganic material membrane which is thinner than the conventional membranes can be formed.

BRIEF DESCRIPTION OF DRAWINGS

FIG. 1 A sectional figure showing the process of Example 1.

FIG. 2 A sectional figure and a plane figure showing the process (continued) of Example 1.

FIG. 3 A sectional figure showing the process of Example 2.

FIG. 4 A sectional figure showing the process (continued) of Example 2.

FIG. 5 A sectional figure showing the process (continued) of Example 2.

FIG. 6 A sectional figure showing the process of Example 3.

FIG. 7 A sectional figure showing the process (continued) of Example 3.

FIG. 8 A sectional figure showing the process of Example 4.

FIG. 9 A sectional figure showing the process (continued) of Example 4.

FIG. 10 A sectional figure showing the process of Example 5.

FIG. 11 A sectional figure showing the process (continued) of Example 5.

FIG. 12 A schematic sectional view of a DNA sequencer using the invention.

DESCRIPTION OF EMBODIMENTS

In all the drawings for explaining the embodiments, components having a same function are indicated by a same reference sign, and the repeated description thereof is avoided as much as possible. The embodiments of the invention are explained in detail below based on the drawings.

The invention should not be construed as being limited to the description of the embodiments shown below. One skilled in the art would easily understand that the specific structures can be modified in the scope which does not depart from the idea or the purpose of the invention.

The terms "first", "second", "third" and the like in this description and the like are given to identify the constituent features but do not necessarily limit the numbers or the orders. Also, the numbers for identifying the constituent features are used independently in each context, and a number used in a context does not always indicate the same structure in another context. Moreover, a constituent feature identified by a number should not be prevented from also having the function of a constituent feature identified by another number.

To facilitate the understanding of the invention, the position, the size, the shape, the range and the like of each component shown in the drawings and the like do not always indicate the actual position, size, shape, range and the like. Thus, the invention should not be limited to the positions, the sizes, the shapes, the ranges and the like disclosed in the drawings and the like.

The publications, the patents and the patent applications cited in this description constitute a part of the explanation in this description as they are.

In this description, a constituent feature that is in the singular also includes the plural unless otherwise specifically indicated clearly in the context.

Example 1

The production process of an Example of the invention is explained using FIG. 1 and FIG. 2.

The first half of the process is explained in FIG. 1.

A $SiO_2$ film 101 is formed on a Si substrate 100. The thickness of the Si substrate is for example 725 μm. The thickness of the $SiO_2$ film 101 is for example 150 nm. A SiN film 102 is formed on the back surface of the Si substrate 100. The thickness of the SiN film 102 is for example 200 nm (FIG. 1(A)).

A resist (not shown in the figure) is applied to the $SiO_2$ film 101, and a hole pattern having a major axis or a length of 100 nm or less for example is formed in the resist using a lithography technique. By dry etching the $SiO_2$ film 101 using the resist as a mask and removing the resist, a hole pattern of the $SiO_2$ film in which the Si substrate is exposed is formed (FIG. 1(B)).

A resist (not shown in the figure) is applied to the back surface, and a pattern of a square hole of 1000 μm to 1100 μm square is formed in the resist using a lithography technique. By dry etching the SiN film 102 using the resist as a mask, a hole pattern of the SiN film in which the back surface of the Si substrate is exposed is formed (FIG. 1(C)).

The second half of the process is explained in FIG. 2 following FIG. 1.

A SiN film 103 is formed on the surface of the $SiO_2$ film 101 or the exposed Si substrate 100. The thickness is for example around 0.3 nm-10 nm. When the film is formed with a thickness as small as possible which at least keeps its film structure, the accuracy as a sensor increases. To improve the production efficiency, the yield rate and the like, the thickness may be around 1.0 nm or more. In this Example, the thickness is less than 5 nm. As the method for forming the film, for example, LP-CVD (Low Pressure Chemical Vapor Deposition) is used (FIG. 2(D)).

By wet etching using an aqueous TMAH (Tetramethylammonium hydroxide) solution, the Si substrate is etched from the back surface. In the above manner, a thin film membrane region 200 is formed (FIG. 2(E)).

A plane figure of the finished device seen from the direction of an arrow 202 in the figure is shown in the lower half of FIG. 2(E). The rectangular thin film membrane region 200 is formed in the middle of the rectangular device. In this description, a region 201 where the underlying substrate 100 has been removed is called a membrane region or a membrane, and a region formed by the thin film in the membrane region 201 (in this Example, a part 200 formed by the SiN film 103) is called a thin film membrane region (or part) for convenience. Here, the external form of the device is for example of approximately 1.5 to 2.0 mm square. The size of the membrane region 201 is for example approximately 50 to 100 μm square. Although the device is rectangular in the example of the figure, the shape is not particularly limited to this shape. Also, one membrane region is formed in one device in the example of the figure, a plurality of membrane regions may be formed in one device.

By the above process, the area of the thin film membrane region 200 can be reduced to an area having a major axis or a length of 100 nm or less. This is because the size of the thin film membrane region 200 is defined by the size of the patterning region in FIG. 1(B). With respect to the size of the patterning region in (FIG. 1(B)), a small pattern having a major axis or a length of 50 nm or less can be formed when the latest EB lithography technique or the ArF lithography technique is used. Because the region of the thin film membrane becomes very small, the possibility of unavoidable defects in the membrane (a weak spot due to the failure of binding between the atoms and the like or a pinhole) which are caused when the membrane is formed becomes lower. Thus, a thinner membrane with excellent quality can be formed.

Although the aqueous TMAH solution comes into direct contact with the thin film membrane part when the thin film membrane part is formed, the aqueous TMAH solution does not etch the SiN film formed using LP-CVD. Thus, when the thin film membrane part is formed, a damage which reduces or breaks the thin film membrane part is not caused. Accordingly, a thinner membrane part can be formed.

By this process, the film 103 is also formed on the wall of the hole of the film 101 formed by dry etching. Using this device, electric measurement is conducted in an aqueous solution after forming a nanopore in the thin film membrane part. When the wall of the film 101, which has been damaged by dry etching, is exposed at this point, the electric charge is apt to be captured or lost on the surface of the wall, resulting in the noise of the measurement. Thus, by covering the wall of the film 101, which has been damaged by dry etching, with the film 103 as in this Example, the frequency of capture or loss of the electric charge on the surface of the wall can be reduced, and the noise of the measurement can be reduced.

The smallest thickness of the conventional SiN membrane thicknesses which have been known is 5 nm (NPL 2). However, according to our experiment, a membrane which was thinner than 5 nm could be formed as a result of the formation of a membrane using the process of the invention. Accordingly, an effect of the use of this process, namely reduction in the thickness of the membrane, has been confirmed.

The film 101 may be formed with a material other than a $SiO_2$ film as long as the material is not etched or is not easily etched with the aqueous TMAH solution. Examples thereof include a SiN film, a laminate film of a SiN film and a $SiO_2$ film or the like.

The film 102 may be formed with a material other than a SiN film as long as the material is not etched or is not easily etched with the aqueous TMAH solution. Examples thereof include a $SiO_2$ film, a laminate film of a SiN film and a $SiO_2$ film or the like.

The film 103 may be formed with a material other than SiN as long as the material is not etched with the aqueous TMAH solution. Examples thereof include one selected from $HfO_2$, $HfAlO_x$, $ZrAlO_x$, $Ta_2O_5$, SiC, SiCN and a carbon film, a synthetic material containing at least one selected therefrom and the like.

For precise analysis of DNA and the like, which is a supposed application of this Example, it is desirable that the thin film membrane part is formed thinly. Thus, it is important to select a material and an etching method which do not damage the thin film membrane part.

In this regard, that a material is not easily etched does not mean that no change by the aqueous solution is acceptable at all, but it is sufficient that the etching rate is different enough from that of the substrate 100 in the production process.

During wet etching with the aqueous TMAH solution, the aqueous TMAH solution sometimes enters the film from a scratch or a defect (a scratch or a defect caused during the process of producing the device) or the like in the film on the front surface of the Si wafer, and the surface at the front side of the Si substrate sometimes becomes rough. To prevent this, protecting the surface with an organic protective film or the like during wet etching with the aqueous TMAH solution and removing the organic protective film with acetone after etching are effective. As the organic protective film, for example, ProTEK (registered trademark) B3primer and ProTEK (registered trademark) B3 of Brewer Science, Inc. and the like are used.

In this process, it is not necessary to conduct a high-temperature process after forming the film 103, which forms the thin film membrane part. Accordingly, even when the film has a low crystallization temperature and has poor performance due to increased leak current in the crystallized state although the film has excellent insulation performance and excellent quality in the amorphous state, like $HfO_2$, the film can be used without being crystallized as a material of a thin film membrane with excellent quality. In a process in which another film is formed after forming a part that becomes the thin film membrane, however, $HfO_2$ is crystallized because the temperature for forming the other film is generally high.

Example 2

In Example 1, a small membrane region can be formed using a latest lithography technique for dry etching as shown in FIG. 1(B). However, a process using latest EB lithography or ArF lithography is expensive, and especially the throughput of EB lithography is poor because it takes time to draw a pattern. Moreover, because the apparatus is also expensive, the device can be produced only by limited semiconductor process lines. Accordingly, a method for forming the membrane device at lower cost and at high throughput is shown in this Example using FIG. 3 to FIG. 5.

The first half of the process is explained in FIG. 3.

The process up to the process of FIG. 1(B) is similar to that of Example 1. To form the hole pattern of the film 101, for example, exposure by lithography using inexpensive i-line and dry etching are used. The size of the opening is for example 500 nm×500 nm. Then, a $SiO_2$ film 104 having a thickness of 220 nm is formed (FIG. 3(A)).

The $SiO_2$ film 104 on the surface is etched back by dry etching, and a side wall is formed. Then, the region of the exposed Si substrate becomes a very small region of approximately 60 nm×60 nm (FIG. 3(B)).

The process is explained in FIG. 4 following FIG. 3.

A resist is applied to the back surface, and a pattern of a square hole of 1000 μm to 1100 μm square is formed in the resist using a lithography technique. By dry etching the SiN film 102 using the resist as a mask, a hole pattern of the SiN film in which the back surface of the Si substrate is exposed is formed (FIG. 4(C)).

A SiN film 105 is formed. The thickness is for example around 0.3 nm-10 nm. As the method for forming the film, for example, LP-CVD (Low Pressure Chemical Vapor Deposition) is used (FIG. 4(D)).

The process is explained in FIG. 5 following FIG. 4.

By wet etching using an aqueous TMAH (Tetramethylammonium hydroxide) solution, the Si substrate is etched from the back surface (FIG. 5(E)).

By this method, a smaller thin film membrane region can be formed at low cost. Also, the region of the thin film membrane can be made smaller than the limit of the formation of a small pattern using a lithography technique. Thus, the method is advantageous for forming a thin film membrane.

The film 101 may be formed with a material other than a $SiO_2$ film as long as the material is not etched or is not easily etched with the aqueous TMAH solution. Examples thereof include a SiN film, a laminate film of a SiN film and a $SiO_2$ film or the like.

The film 102 may be formed with a material other than a SiN film as long as the material is not etched or is not easily etched with the aqueous TMAH solution. Examples thereof include a $SiO_2$ film, a laminate film of a SiN film and a $SiO_2$ film or the like.

The film 104 may be formed with a material other than a $SiO_2$ film as long as the material is not etched or is not easily etched with the aqueous TMAH solution. Examples thereof include a SiN film, a laminate film of a SiN film and a $SiO_2$ film or the like.

The film 105 may be formed with a material other than SiN as long as the material is not etched with the aqueous TMAH solution. Examples thereof include $HfO_2$, $HfAlO_x$, $ZrAlO_x$, $Ta_2O_5$, SiC, SiCN, a carbon film, synthetic materials thereof and the like.

During wet etching with the aqueous TMAH solution, the aqueous TMAH solution sometimes enters the film from a scratch or a defect (a scratch or a defect caused during the process of producing the device) or the like in the film on the front surface of the Si wafer, and the surface at the front side of the Si substrate sometimes becomes rough. To prevent this, protecting the surface with an organic protective film or the like during wet etching with the aqueous TMAH solution and removing the organic protective film with acetone after etching are effective. As the organic protective film, for example, ProTEK (registered trademark) B3primer and ProTEK (registered trademark) B3 of Brewer Science, Inc. and the like are used.

Example 3

After forming a nanopore in the membrane, the chambers above and below the membrane are filled with an aqueous ionic solution, and DNA to be detected is supplied to one of the chambers. Electrodes are provided in such a manner that the electrodes are immersed in the aqueous solution in the chambers above and below the membrane. The DNA is caused to pass through the nanopore by causing a potential difference between the electrodes. By measuring the change in the current at this point, the structural characteristics of the DNA and the nucleotide sequence are determined. During the measurement by causing a potential difference between the electrodes, it is preferable that localized concentration of electric field to the thin film membrane part does not occur. This is because localized concentration of electric field promotes the breakage of the membrane.

In this Example explained with FIGS. 6 and 7, a process and a device structure which avoid localized concentration of electric field to the thin film membrane are shown.

The first half of the process is explained in FIG. 6.

During dry etching in FIG. 1(B) of Example 1, the Si substrate 100 is not exposed by etching. For example, around 110 nm of the $SiO_2$ film 101 having a thickness of 150 nm is removed by etching, and the $SiO_2$ film of around 40 nm is left on the Si substrate (FIG. 6(A)).

The $SiO_2$ film 101 is etched with an aqueous HF solution, and the Si substrate is exposed (FIG. 6(B)).

The second half of the process is explained continuously in FIG. 7.

A resist is applied to the back surface, and a pattern of a square hole of 1000 μm to 1100 μm square is formed in the resist using a lithography technique. By dry etching the SiN film 102 using the resist as a mask, a hole pattern of the SiN film in which the back surface of the Si substrate is exposed is formed (FIG. 7(C)).

A SiN film 106 is formed. The thickness is for example around 0.3 nm-10 nm. As the method for forming the film, for example, LP-CVD (Low Pressure Chemical Vapor Deposition) is used (FIG. 7(D)).

By wet etching using an aqueous TMAH (Tetramethylammonium hydroxide) solution, the Si substrate is etched from the back surface (FIG. 7(E)).

By removing the $SiO_2$ film 101 by wet etching and exposing the surface of the substrate, the part indicated with dashed circles in FIG. 7(E), namely the edge part of the thin film membrane, becomes rounded. Thus, when an electric field is applied to the thin film membrane part, the degree of concentration of the electric field to this part is reduced. Thus, the possibility of the breakage of the membrane during the measurement, namely while an electric field is applied to the membrane, can be further reduced.

SiN may be used for the film 101 as well as $SiO_2$. In this case, a heated aqueous phosphoric acid solution is used for wet etching in (FIG. 6(B)). At this point, it is preferable that the film 102 is a SiN film that is sufficiently thicker than the film 101 or a $SiO_2$ film so that the film 102 on the back surface of the Si substrate is not lost by etching.

The film 102 may be formed with a material other than a SiN film as long as the material is not etched or is not easily etched with the aqueous TMAH solution. Examples thereof include a $SiO_2$ film, a laminate film of a SiN film and a $SiO_2$ film or the like.

The film 106 may be formed with a material other than SiN as long as the material is not etched with the aqueous TMAH solution. Examples thereof include $HfO_2$, $HfAlO_x$, $ZrAlO_x$, $Ta_2O_5$, SiC, SiCN, a carbon film, synthetic materials thereof and the like.

During wet etching with the aqueous TMAH solution, the aqueous TMAH solution sometimes enters the film from a scratch or a defect (a scratch or a defect caused during the process of producing the device) or the like in the film on the front surface of the Si wafer, and the surface at the front side of the Si substrate sometimes becomes rough. To prevent this, protecting the surface with an organic protective film or the like during wet etching with the aqueous TMAH solution and removing the organic protective film with acetone after etching are effective. As the organic protective film, for example, ProTEK (registered trademark) B3primer and ProTEK (registered trademark) B3 of Brewer Science, Inc. and the like are used.

Example 4

A process in the case where the film 101 in Example 3 has a laminate structure of $SiO_2$ and SiN is shown using FIG. 8 and FIG. 9.

The first half of the process is explained in FIG. 8.

The $SiO_2$ film 101 is formed on the Si substrate 100. The thickness of the Si substrate is for example 725 μm. The thickness of the $SiO_2$ film 101 is for example 150 nm. The SiN film 102 is formed on the back surface of the Si substrate 100. The thickness of the SiN film 102 is for example 200 nm. A SiN film 107 is formed on the film 101. The thickness of the film 107 is for example 100 nm (FIG. 8(A)).

A resist is applied to the SiN film 107, and a hole pattern having a diameter of 100 nm or less for example is formed in the resist using a lithography technique. By dry etching the SiN film 107 using the resist as a mask and removing the resist, a hole pattern in which the SiO$_2$ film 101 remains at the bottom of the pattern is formed (FIG. 8(B)).

The SiO$_2$ film 101 is etched with an aqueous HF solution, and the Si substrate is exposed (FIG. 8(C)).

The second half of the process is explained continuously in FIG. 9.

A resist is applied to the back surface, and a pattern of a square hole of 1000 μm to 1100 μm square is formed in the resist using a lithography technique. By dry etching the SiN film 102 using the resist as a mask, a hole pattern of the SiN film in which the back surface of the Si substrate is exposed is formed (FIG. 9(D)).

A SiN film 108 is formed. The thickness is for example around 0.3 nm-10 nm. As the method for forming the film, for example, LP-CVD (Low Pressure Chemical Vapor Deposition) is used (FIG. 9(E)).

By wet etching using an aqueous TMAH (Tetramethylammonium hydroxide) solution, the Si substrate is etched from the back surface (FIG. 9(F)).

In this manner, the part indicated with dashed circles in (FIG. 9(F)), namely the edge part of the thin film membrane, becomes rounded. Thus, when an electric field is applied to the thin film membrane part, the degree of concentration of the electric field to this part is reduced. Thus, the possibility of the breakage of the membrane during the measurement, namely while an electric field is applied to the membrane, can be further reduced.

The film 102 may be formed with a material other than a SiN film as long as the material is not etched or is not easily etched with the aqueous TMAH solution. Examples thereof include a SiO$_2$ film, a laminate film of a SiN film and a SiO$_2$ film or the like.

The film 108 may be formed with a material other than SiN as long as the material is not etched with the aqueous TMAH solution. Examples thereof include HfO$_2$, HfAlO$_x$, ZrAlO$_x$, Ta$_2$O$_5$, SiC, SiCN, a carbon film, synthetic materials thereof and the like.

During wet etching with the aqueous TMAH solution, the aqueous TMAH solution sometimes enters the film from a scratch or a defect (a scratch or a defect caused during the process of producing the device) or the like in the film on the front surface of the Si wafer, and the surface at the front side of the Si substrate sometimes becomes rough. To prevent this, protecting the surface with an organic protective film or the like during wet etching with the aqueous TMAH solution and removing the organic protective film with acetone after etching are effective. As the organic protective film, for example, ProTEK (registered trademark) B3primer and ProTEK (registered trademark) B3 of Brewer Science, Inc. and the like are used.

When the SiO$_2$ film 101 is etched in (FIG. 8(C)), the etching rate of the SiN film 107 is lower than the etching rate of the SiO$_2$ film 101. Thus, in the final (FIG. 9(F)) structure, basically, the thickness of the part other than the thin film membrane region (the total thickness of the film 101, the film 107 and the film 108) can be kept thicker than that obtained by the process of Example 3.

When the thickness of the part other than the thin film membrane region (the total thickness of the film 101, the film 107 and the film 108) increases, the mechanical strength of the whole membrane (the region including the film of the part which is not the thin film membrane part and which is not directly on the Si substrate) enhances. Thus, the yield rate of the produced membrane and the resistance improve.

Example 5

As described in the Examples above, to prevent the surface at the front side of the Si substrate from becoming rough during wet etching with the aqueous TMAH solution, protecting the surface with an organic protective film or the like and removing the organic protective film with acetone after etching are effective. As the organic protective film, for example, ProTEK (registered trademark) B3primer and ProTEK (registered trademark) B3 of Brewer Science, Inc. and the like are used. In this Example, a process for more fully removing the organic protective film is shown in FIG. 10 and FIG. 11.

The first half of the process is explained in FIG. 10.

After the process up to (FIG. 2(D)) of Example 1 is finished, a silicon film (a polysilicon or amorphous silicon film) 109 of for example 100 nm is formed (FIG. 10(A)).

An organic protective film 110 is applied on the surface (FIG. 10(B)).

The second half of the process is explained in FIG. 11.

By wet etching using an aqueous TMAH (Tetramethylammonium hydroxide) solution, the Si substrate is etched from the back surface (FIG. 11(C)).

The organic protective film 110 is removed with acetone (FIG. 11(D)).

The silicon 109 is removed by wet etching using an aqueous TMAH (Tetramethylammonium hydroxide) solution (FIG. 11(E)).

The organic protective film 110 is applied on the silicon 109. Thus, by wet etching the silicon after removing the organic protective film 110, the slightly remaining organic protective film 110 on the wafer surface that could not be removed can be removed together. Accordingly, the yield rate and the quality of the formed membrane device improve as compared to those of the membrane device obtained when the organic protective film is applied directly on the thin film membrane part (the film 103) and then removed.

The film 101 may be formed with a material other than a SiO$_2$ film as long as the material is not etched or is not easily etched with the aqueous TMAH solution. Examples thereof include a SiN film, a laminate film of a SiN film and a SiO$_2$ film or the like.

The film 102 may be formed with a material other than a SiN film as long as the material is not etched or is not easily etched with the aqueous TMAH solution. Examples thereof include a SiO$_2$ film, a laminate film of a SiN film and a SiO$_2$ film or the like.

The film 103 may be formed with a material other than SiN as long as the material is not etched with the aqueous TMAH solution. Examples thereof include HfO$_2$, HfAlO$_x$, ZrAlO$_x$, Ta$_2$O$_5$, SiC, SiCN, a carbon film, synthetic materials thereof and the like.

Example 6

An aqueous KOH solution is used as the aqueous solution used for Si etching in addition to an aqueous TMAH solution. An aqueous KOH solution hardly etches a SiN film formed using LP-CVD. Thus, when the membrane thin film part is formed with a SiN film formed using LP-CVD in the Examples above, an aqueous KOH solution may be used instead of the aqueous TMAH solution. In this case, to prevent the films other than the thin film membrane part from being removed, the parts which come into contact with the aqueous KOH solution are preferably formed with SiN if possible.

Example 7

An Example in which any of the devices formed in Examples 1 to 6 is used as a sensor (for example, a DNA sequencer) is explained.

FIG. 12 is a sectional view of a DNA sequencer composed using the device produced in Example 1.

A hole (nanopore) 1200 for example having a size equivalent to that of DNA (for example, around 1-10 nm) is provided in the thin film membrane region of any of the devices formed in Examples 1 to 6. An upper chamber 1210 and a lower chamber 1220 of the thin film membrane region are filled with an aqueous solution, and electrodes 1230 are provided in the chambers in such a manner that the electrodes 1230 are in contact with the aqueous solution. DNA to be measured is supplied to one of the chambers. The DNA is moved by electrophoresis caused by a potential difference applied between the electrodes in the chambers so that the DNA passes through the nanopore, and the change with time in the ion current flowing between the electrodes is measured. The structural characteristics of the DNA and the nucleotide sequence can be thus determined. This is also effective in obtaining the structural characteristics of not only DNA but also of various molecules, especially biomolecules.

With respect to the nanopore, a small pinhole can be formed in the thin film membrane region by applying voltage stress to the membrane in an aqueous ionic solution and causing dielectric breakdown. In another method, the nanopore can be formed by etching the thin film membrane region using the condensed electron beam.

In each of the devices formed in Examples 1 to 6, the inner wall of the upper chamber can be covered with the thin film which extends from the thin film membrane region. The inner wall of the lower chamber can be formed with the cavity created by etching the silicon substrate.

The invention is not limited to the above embodiments and includes variants of various kinds. For example, a component of an Example can be replaced with a component of another Example, and a component of an Example can be added to a component of another Example. Moreover, a component of an Example can be deleted or replaced with a component of another Example, or a component of another Example can be added.

INDUSTRIAL APPLICABILITY

The invention can be used for various devices for analysis.

REFERENCE SIGNS LIST

100: Si substrate
101: film (SiO$_2$ film or the like)
102: film (SiN film or the like)
103: film (SiN film or the like)
104: film (SiO$_2$ film or the like)
105: film (SiN film or the like)
106: film (SiN film or the like)
107: film (SiN film)
108: film (SiN film or the like)
109: film (silicon film)
110: film (organic protective film)

The invention claimed is:

1. A method for forming a biomolecular structure analysis device comprising forming a nanopore sequencing membrane by forming a first film on a surface of a substrate, wherein the surface is Si,
   then forming a hole in the first film in such a manner that the surface of the substrate is exposed,
   then forming a second film thinner than 5 nm on the first film and on the surface of the substrate and then etching the substrate with a solution which does not remove the second film.

2. The method according to claim 1 wherein the forming the second film comprises using at least one selected from SiN, HfO2, HfAlOx, ZrAlOx, Ta2O5, SiC, SiCN and a carbon film or a substance containing at least one selected therefrom as the material of the second film.

3. The method according to claim 1 wherein the first film is composed of SiN or SiO2.

4. The method according to claim 1, wherein the aqueous solution used for etching the substrate is an aqueous TMAH solution.

5. The method according to claim 1, wherein the aqueous solution used for etching the substrate is an aqueous KOH solution.

6. The method according to claim 1, wherein wet etching is used in the step of forming the hole in the first film in such a manner that the surface of the substrate is exposed.

7. The method according to claim 1 wherein the forming the nanopore sequencing membrane further comprises:
   forming a third film after forming the hole in the first film in such a manner that the surface of the substrate is exposed, the third film formed on an opposite side of the substrate of the first film,
   then forming a side wall of the third film on a wall of the first film by etching back the third film,
   then forming the second film on the first film, on the third film and on the surface of the substrate and
   then etching the substrate with the solution which does not remove the second film.

8. The method of claim 1, wherein the forming a hole in the first film in such a manner that the surface of the substrate is exposed comprises forming a hole pattern having a patterning region with a major axis or length of 50 nm or less.

9. A biomolecular structure analysis device comprising a nanopore sequencing membrane supported with a substrate wherein:
   the surface of the substrate is Si,
   the membrane has a structure in which the substrate is not right under the membrane,
   the membrane is formed with a film of at least two layers or more,
   a part of the membrane has a thin film membrane region formed with a first film,
   the thin film membrane region is surrounded by a second film which is thicker than the first film,
   the first film is formed also on a wall of the second film,
   the first film is thinner than 5 nm, and
   the substrate is located right under a part of the second film which is outside the membrane.

10. The biomolecular structure analysis device according to claim 9 wherein the material of the first film is at least one selected from SiN, HfO2, HfAlOx, ZrAlOx, Ta2O5, SiC, SiCN and a carbon film or a substance containing at least one selected therefrom.

11. The biomolecular structure analysis device according to claim 9 wherein the material of the second film is SiN, SiO2 or a laminate film of SiN and SiO2.

12. The biomolecular structure analysis device according to claim 9 further comprising a side wall on a wall of the second film, wherein the side wall is formed by etching back a third film after forming the third film.

13. The biomolecular structure analysis of claim 9, wherein the part of the membrane has the thin film membrane region with a patterning region having a major axis or length of 50 nm or less formed with the first film.

* * * * *